US008791283B1

(12) United States Patent
Chong et al.

(10) Patent No.: US 8,791,283 B1

(45) Date of Patent: Jul. 29, 2014

(54) PROCESS FOR FRACTIONATING REFINED TRIGLYCERIDE OIL

(71) Applicant: Malaysian Palm Oil Board (MPOB), Selangor Darul Ehsan (MY)

(72) Inventors: Chiew Let Chong, Kajang (MY); Chee Beng Yeoh, Kajang (MY)

(73) Assignee: Malaysian Palm Oil Board (MPOB), Kajang, Selangor Darul Ehsan (MY)

( * ) Notice: Subject to any disclaimer, the term of this patent is extended or adjusted under 35 U.S.C. 154(b) by 0 days.

(21) Appl. No.: 14/025,685

(22) Filed: Sep. 12, 2013

(30) Foreign Application Priority Data

Apr. 1, 2013 (MY) .......................... PI 2013001144

(51) Int. Cl.
*C07C 51/43* (2006.01)

(52) U.S. Cl.
USPC .......................................................... 554/211

(58) Field of Classification Search
CPC .................................................... C11B 7/0075
USPC .......................................................... 554/221
See application file for complete search history.

(56) References Cited

U.S. PATENT DOCUMENTS 4,795,569 A 1/1989 Higuchi et al.
5,045,243 A 9/1991 Kuwabara et al.

FOREIGN PATENT DOCUMENTS

EP 1028159 A1 * 8/2000 ................ C11B 7/00

* cited by examiner

*Primary Examiner* — Deborah D Carr
(74) *Attorney, Agent, or Firm* — Maschoff Brennan

(57) ABSTRACT

The present invention relates to a process for fractioning refined triglyceride oil. The process according to the present invention attains a reproducible crystallization by introducing a controlled temperature profile and ensuing crystal development that reduce the amount of entrapped olein inside the crystals or crystal aggregates. The process of the present invention may be used to fractionate refined and or refined, bleached and deodorized vegetable oils especially refined and or refined, bleached and deodorized palm oil.

4 Claims, No Drawings

PROCESS FOR FRACTIONATING REFINED TRIGLYCERIDE OIL

FIELD OF INVENTION

The present invention relates to a process for fractionating refined triglyceride oil. More particularly, it relates to a process for fractionating refined and/or refined, bleached and deodorized (RBD) triglyceride oil obtained from edible vegetable oils which is semi solid ambient at temperature of between 0 to 40° C.

BACKGROUND OF INVENTION

Triglyceride oils contain undesirable minor components or impurities including free saturated fatty acids, such as palmitic or stearic acids, and other suspended matter that, unless removed, render the oil commercially unsuitable in that they produce a soapy taste or a strong flavour. Such unrefined oils are generally refined by one or several of the following steps: degumming, neutralizing or alkali refining to reduce the fatty acid content thereof, bleaching, dewaxing and deodorization.

The main source of haziness and discoloration in triglyceride oil is the presence of crystallized triglycerides with saturated fatty acids such as palmitic or stearic acids. These triglycerides with saturated fatty acids crystallize and agglomerate producing a haze and also precipitate creating a turbid product. Another cause of haziness in the oil is the presence of other dispersed solids like protein and mucilaginous materials of microscopic size. Precipitated matter, such as proteins, can cause deterioration of the oil. When these microscopic materials agglomerate they become visible and produce unsightly haze in the final oil product. The haziness due to crystallized saturated fat is not very aesthetically pleasing. This is detrimental, particularly in cosmetics and pharmaceuticals, since it is important for the oil to be very clear and translucent to be appealing to customers. In the field of oil processing, fractionation almost always refers to the mechanical separation of the liquid from the solid, crystallized, constituents of a given oil. The split between liquid and solid fractions depends on the temperature at which crystallization is conducted.

Fractionation is a process that has been known in industrial from for more than a century. Before then, the olein and stearin fractions had been separated by settling, using only the force of gravity to bring about a separation between the heavier solid phase and the lighter liquid phase. Naturally this method of fractionation left the settled solid phase containing large quantities of entrained or trapped liquid oil, almost certainly more than 15%.

In the latter years a process of this type, using only indirect cooling of the oil but separating liquid from solid by filter or centrifuge, become known as “dry fractionation”.

Vegetable oils especially palm oil is fractionated in one- or two-stages by utilizing the different in melting points of respective components, there have been known for instances, solvent fractionation using organic solvent such as acetone, hexane, or the like, detergent fractionation using a surfactant, dry fractionation, sweating and the like.

Among these, solvent fractionation is advantageous because fractionation can be carried out precisely. However, on the other hand, this is dangerous, since a flammable solvent is used, and also requires high production costs. In addition, solvent fractionation is not the most effective process for the fractionation of raw materials such as coconut oil, palm kernel oil and fat.

The method of detergent fractionation has inferior precision of fractionation and its products have inferior quality in comparison with those fractionated using solvent fractionations. Furthermore, separation of oil from an aqueous solution containing a surfactant and treatment of waste water containing a surfactant are troublesome and incomplete.

The method of dry fractionation requires expensive crystallization tank facilities. In addition, productivity, fractionation efficiency and quality of a product are inferior to those of the above two methods.

Application of the sweating method is limited to certain kinds of fats and oils. That is, it is employed for removing a wax but is not suitable for fractionation of oils or fats.

Dry fractionation involves the heating up of palm oil to a temperature of between 50 to 55° C., cooling the oil to between 30 to 40° C. followed by further cooling of the oil to the final fractionation temperature of between 20 to 25° C. The crystallizer is then held at this temperature for a number of hours depending on the type and characteristics of the olein and stearin desired. The crystallized slurry is then filtered under a pressure to obtain the olein and stearin fractions. The yield of olein and stearin obtained is between 75 to 80% and 20 to 25%, respectively. If the holding times, the number of fractionation steps or the filtration pressure is varied the characteristics of the olein and stearin obtained could be altered. The iodine value (IV) of the olein obtained is about 56 for a single fractionation of around 10 hours holding time at the final fractionation temperature and a filtration pressure of 3 to 5 bars.

Dry fractionation of refined palm oil using the conditions stated above is deemed to be difficult to control due to the presence of gums and other impurities which will interfere with the crystallization of the oil during the fractionation process.

At present the fractionation of refined palm oil is only carried out using the wet detergent process. An aqueous solution of sodium lauryl sulphate is added and the mixture is cooled to crystallize the stearin. The slurry is then centrifuged to separate the solid from the liquid phase. Water is then removed from the olein phase and the detergent removed at the same time. This process is completely different from that of dry fractionation. It may be very difficult to completely remove all the detergent from the olein phase and there may be trace quantities of the detergent left. In view of the mounting emphasis on food safety in the future, this process will be less and less appealing.

U.S. Pat. No. 4,795,569 to Higuchi et al. describes a process in which the oil is introduced into a filter chamber and allowed to crystallize inside that chamber by circulating a coolant such as water through the space between the membrane and a filter frame. However, this process requires the filter cloth to be sealed first with a coagula of the material to be treated. This makes it a lengthy process that makes inefficient use of the expensive membrane press.

Accordingly, an improvement has been described in U.S. Pat. No. 5,045,243 to Kuwabara et al. in which the oil or fat to be fractionated is first of all solidified in trays to form solid blocks which are then crushed to yield a pumpable paste that is then introduced into a membrane press to separate this paste into an olein fraction and a stearin fraction. The solidification process is commonly carried out in cooling tunnels. However, these have the disadvantage that the oil is exposed to the air while being and that it is virtually impossible to control the rate of cooling inside the individual trays.

Therefore, European Patent Application 1028159 by Yoneda et al. disclosed a stationary crystallisation. The oil or fat to be fractionated is not solidified into a solid block, but the crystallisation process is halted when the partially crystallised mass is still sufficiently fluid to be pumped into the membrane filter press. However, this means that the material to be fractionated has to be diluted with olein before being cooled.

SUMMARY OF INVENTION

It is therefore an object of the present invention to provide a process for fractionation of vegetable oil especially palm oil which can improve the efficiency of dry fractionation.

A further object of the present invention is to attain a reproducible crystallization by introducing controlled temperature profile during cooling and the ensuing crystal development.

Another object of the present invention is to provide an improved process of dry fractionation that reduce the amount of entrained or entrapped olein inside the crystals or crystal aggregates.

It is also an object of the present invention to provide a process of dry fractionation that produces a favourable crystal form to ease the filtration process and minimal olein entrapment.

According to the present invention, the process for fractionating refined triglyceride oil which is semi solid at a temperature of between 0 to 40° C., wherein the triglyceride oil is obtained from an edible vegetable oil, the process includes the steps of (a) heating the triglyceride oil to a temperature range of between 55 to 70° C. for a period of about 1 minute to 3 hours, (b) cooling the triglyceride oil obtained from step (a) to a temperature range of between 20 to 30° C. for a period of about 1 minute to 5 hours such that the triglyceride oil is at least partially crystallized thereby forming crystallized slurries, (c) warming the crystallized triglyceride oil from step (b) to a temperature in the range of between 22 to 33° C. for a period of about 1 minute to 3 hours, (d) cooling the triglyceride oil obtained from step (c) to a temperature range of between 10 to 30° C. for a period of about 1 minute to 65 hours and (e) removing the crystallized slurries which is at a temperature in the range of between 10 to 30° C. for a period of about 1 minute to 65 hours.

The method according to the present invention, wherein said heating the triglyceride oil of step (a) results in said triglyceride oil having a temperature in the range of approximately 55 to 70° C. for a period in the range of about 1 minute to 3 hours.

Cooling the triglyceride oil of step (b) results in said triglyceride oil having a temperature in the range of 28 to 40° C. for a period in the range of about 1 minute to 3 hour and further cooling of the triglyceride oil results in said triglyceride oil having a temperature in the range of about 20 to 28° C. for a period in the range of about 1 minute to 5 hours.

Besides, warming the triglyceride oil, step (d) is carried out at a temperature in the range of about 20 to 30° C. to a temperature in the range of 22 to 33° C. for a period in the range of about 1 minute to 3 hours.

The oil is then cooled to a temperature (e) in the range of 10 to 30° C. in 1 minute to 3 hours.

The further crystallizing of step (f) is performed at a temperature in the range of about 10 to 30° C. for a period in the range of about 1 minute to 65 hours.

DETAILED DESCRIPTION OF THE PREFERRED EMBODIMENTS

According to the present invention, there is provided a process for fractionating refined triglyceride oil which is semi solid at a temperature of between 0 to 40° C., wherein the triglyceride oil is obtained from an edible vegetable oil, the process includes the steps of (a) heating the triglyceride oil to a temperature range of between 55 to 70° C. for a period of about 1 minute to 3 hours, (b) cooling the triglyceride oil obtained from step (a) to a temperature range of between 20 to 30° C. for a period of about 1 minute to 5 hours such that the triglyceride oil is at least partially crystallized thereby forming crystallized slurries, (c) warming the crystallized triglyceride oil from step (b) to a temperature in the range of between 22 to 33° C. for a period of about 1 minute to 3 hours, (d) cooling the triglyceride oil obtained from step (c) to a temperature range of between 10 to 30° C. for a period of about 1 minute to 65 hours and (e) removing the crystallized slurries which is at a temperature in the range of between 10 to 30° C. for a period of about 1 minute to 65 hours.

In the preferred embodiment of the present invention, refined palm oil is heated to a temperature of approximately 50-70° C. and held for a period in the range of about 1 minute to 3 hour at this temperature to thoroughly destroy all traces of previous thermal history.

The heated oil is then cooled to a temperature in the range of 20 to 30° C. for a period in the range of about 1 minute to 3 hour. The oil is then further cooled to a fractionation temperature of between 20 to 30° C. The oil is then held at this fractionation temperature until the oil crystals are seen to appear. The crystallizing slurry is then allowed to crystallize further for a period of about 1 minute to 5 hours.

After that, the temperature of the crystallizing slurry is increased to a temperature in the range of 22 to 33° C. Upon reaching this temperature, the crystallizing slurry is kept at this temperature for a period of 1 minute to 3 hours. After this period the temperature of the crystallizing slurry is lowered to a temperature in the range of 10 to 30° C. and held for a period of 1 minute to 65 hours.

The crystallizing slurry is then filtered under a pressure of 3 to 60 bars in a membrane or any other type of filter or filtration to obtain the olein and stearin fractions.

The present invention can be distinguished from the previous state of the art is in the step whereby the temperature of the crystallizing slurry is increased from the final fractionation temperature in the range of 20 to 30° C. after the appearance of the oil crystals and a holding period of about 1 minute to 5 hours, to a temperature in the range of 22 to 33° C. where it is held for a period of about 1 minute to 3 hours before the temperature of the said slurry is returned to the final fractionation temperature in the range of 10 to 30° C. and held for 1 minute to 65 hours.

Smaller crystals in the crystallizing slurry will dissolve and grow on the existing larger and harder crystals. This will result in coarse, large and hard crystals, which are easily filtered and are able to withstand the filtration pressure. This will also reduce the amount of entrained or entrapped olein inside the crystals or crystal aggregates. β' (beta-prime) crystals are obtained in the temperature range of 20-35° C. as verified by X-ray diffraction of the crystals obtained for crude palm oil crystals. This is the desired crystal form for easy filtration and minimal olein entrapment. The dry fractionation condition applied in the present invention can be used for the dry fractionation of crude palm oil and their fractions, in the case of multiple fractionations, with olein yield of between 70 to 85% and stearin yield of 15 to 30% from laboratory results for the first fractionation. The IV of the olein obtained from the method according to the present invention is 30 between 56-60 Wij and the IV of the stearin is between 30 to 45 Wij for a single fractionation step with a holding time of around ten hours and using vacuum filtration. If the holding times are extended, the number of fractionations can be increased. The same concepts embodied in this present invention can be applied at each step.

It is to be understood that the present invention may be embodied in other specific forms and is not limited to the sole embodiment described above. However modifications and equivalents of the disclosed concepts such as those which readily occur to one skilled in the art are intended to be included within the scope of the claims which are appended thereto.

EXAMPLE

An experiment was conducted to fractionate a refined triglyceride oil as per the present invention. The steps involved in this process:

(a) heating the triglyceride oil 65° C. for 30 minutes;

(b) cooling the triglyceride oil to 30° C. for 75 minutes;

(c) further cooling the triglyceride oil to 24° C. for 60 minutes until the triglyceride oil is at least partially crystallized thereby forming crystallized slurries;

(d) warming the crystallized triglyceride oil from step (c) to 31° C. for 15 minutes;

(e) cooling the triglyceride oil obtained from step (d) to 24° C. for 10 minutes (f) allowing further crystallizing at 24° C. for 80 minutes; and (g) removing the crystallized slurries.

Results

It is noted that the yield of olein obtained from laboratory vacuum filtration system is 62.5% as compared to the control without steps (d) to (f) where the yield obtained is only 60.1%.

The invention claimed is:

1. A process for fractionating refined triglyceride oil which is semi solid at a temperature of between 0 to 40° C., wherein the triglyceride oil is obtained from an edible vegetable oil, the process includes the steps of:

(a) heating the triglyceride oil to a temperature range of between 55 to 70° C. for a period of about 1 minute to 3 hours;

(b) cooling the triglyceride oil obtained from step (a) to a temperature range of between 20 to 30° C. for a period of about 1 minute to 5 hours such that the triglyceride oil is at least partially crystallized thereby forming crystallized slurries;

(c) warming the crystallized triglyceride oil from step (b) to a temperature in the range of between 22 to 33° C. for a period of about 1 minute to 3 hours;

(d) cooling the triglyceride oil obtained from step (c) to a temperature range of between 10 to 30° C. for a period of about 1 minute to 65 hours; and (e) removing the crystallized slurries which is at a temperature in the range of between 10 to 30° C. for a period of about 1 minute to 65 hours.

2. The process according to claim 1, wherein said vegetable oil is vegetable oil is refined and or refined, bleached and deodorized palm oil, or other refined and or refined, bleached and deodorized vegetable oil either in its natural state or after processing and or modifications.

3. The process according to claim 2, wherein said palm oil is crude palm oil, refined, bleached or deodorized palm oil.

4. The process according to claim 1, wherein said removing of crystallized slurry is conducted using filtration to obtain olein fraction and stearin fraction.

* * * * *